(12) United States Patent
Kim et al.

(10) Patent No.: US 7,915,302 B2
(45) Date of Patent: Mar. 29, 2011

(54) CRYSTAL FORMS OF PYRROLYLHEPTANOIC ACID DERIVATIVES

(75) Inventors: Moon Sung Kim, Seongnam-si (KR); Moo Hi Yoo, Seoul (KR); Jae Keol Rhee, Pyeongtaek-si (KR); Yong Jik Kim, Yongin-si (KR); Seong Jin Park, Seoul (KR); Jun Ho Choi, Yongin-si (KR); Si Young Sung, Yongin-si (KR); Hong Gyu Lim, Seoul (KR); Dae Won Cha, Yongin-si (KR)

(73) Assignee: Dong-A Pharm. Co., Ltd., Seoul (KR)

( * ) Notice: Subject to any disclaimer, the term of this patent is extended or adjusted under 35 U.S.C. 154(b) by 0 days.

(21) Appl. No.: 12/449,867

(22) PCT Filed: Mar. 3, 2008

(86) PCT No.: PCT/KR2008/001218
§ 371 (c)(1),
(2), (4) Date: Sep. 17, 2009

(87) PCT Pub. No.: WO2008/108572
PCT Pub. Date: Sep. 12, 2008

(65) Prior Publication Data
US 2010/0113556 A1 May 6, 2010

(30) Foreign Application Priority Data

Mar. 2, 2007 (KR) .................. 10-2007-0020999
Mar. 3, 2008 (KR) .................. 10-2008-0019764

(51) Int. Cl.
*A61K 31/40* (2006.01)
*C07D 207/30* (2006.01)

(52) U.S. Cl. .......................... 514/423; 548/537
(58) Field of Classification Search ............ 548/537; 514/423
See application file for complete search history.

(56) References Cited

U.S. PATENT DOCUMENTS 5,273,995 A * 12/1993 Roth .................. 514/422
5,969,156 A * 10/1999 Briggs et al. .......... 548/537

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*

* cited by examiner

*Primary Examiner* — Rebecca L Anderson
*Assistant Examiner* — Samantha L Shterengarts
(74) *Attorney, Agent, or Firm* — The Nath Law Group; Joshua B. Goldberg; Mihsuhn Koh

(57) ABSTRACT

The present invention provides novel crystalline forms D1 and D2 of [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemicalcium salt, and hydrates thereof. The crystalline forms D1 and D2 have X-ray powder diffraction peaks described in FIGS. 1 and 3, respectively. Further, the present invention provides processes for preparing the crystalline forms and pharmaceutical compositions comprising the crystalline forms. The crystalline forms can be produced on a commercial scale and exhibit excellent stability.

14 Claims, 4 Drawing Sheets

CRYSTAL FORMS OF PYRROLYLHEPTANOIC ACID DERIVATIVES

This is a National Phase Application filed under 35 USC 371 of International Application No. PCT/KR2008/001218, filed on Mar. 3, 2008, which claims foreign priority benefits under 35 USC 119 of Korean Application No. 10-2007-0020999, filed on Mar. 2, 2007, and which claims foreign priority benefits under 35 USC 119 of Korean Application No. 10-2008-0019764, filed on Mar. 3, 2008, the entire content of each of which is hereby incorporated herein by reference in its entirety.

TECHNICAL FIELD

The present invention relates to novel crystalline forms of [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemicalcium salt as a pyrrole heptanoic acid derivative, hydrates thereof, processes for preparing the crystalline forms, and pharmaceutical compositions comprising the crystalline forms.

BACKGROUND ART

Many pyrrole heptanoic acid derivatives have been synthesized. Of these, [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid is a statin drug whose mechanism of action has been elucidated in detail and is known to be the most therapeutically effective drug available for reducing the concentration of low-density lipoprotein (LDL) as a risk factor of thrombosis. The pyrrole heptanoic acid derivative is currently commercially available in the form of hemicalcium salt trihydrate. The pyrrole heptanoic acid hemicalcium salt is represented by Formula 1:

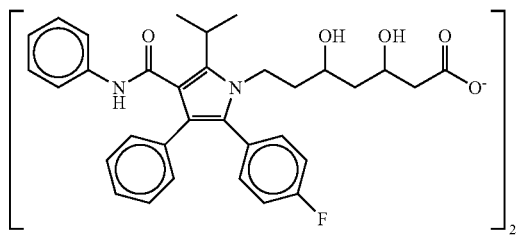

(1)

[R—(R*,R*)]-2-(4-fluorophenyl)-β,δ-dihydroxy-5-(1-methylethyl)-3-phenyl-4-[(phenyl-amino)carbonyl]-1H-pyrrole-1-heptanoic acid was first disclosed in U.S. Pat. No. 4,681,893. U.S. Pat. No. 5,273,995 teaches that the compound of Formula 1 is prepared by crystallization from a brine solution resulting from the transposition of the sodium salt with $CaCl_2$ and further purified by recrystallization from a 5:3 mixture of ethyl acetate and hexane.

Various processes and key intermediates for preparing amorphous forms of the compound' of Formula 1 are found in the literature, for example, U.S. Pat. Nos. 5,003,080, 5,097,045, 5,103,024, 5,124,482, 5,149,837, 5,155,251, 5,216,174, 5,245,047, 5,248,793, 5,280,126, 5,397,792, 5,342,952, 5,298,627, 5,446,054, 5,470,981, 5,489,690, 5,489,691, 5,510,488, 5,998,633 and 6,087,511. However, the amorphous forms have unsuitable filtration and drying characteristics for large-scale production and must be protected from heat, light, oxygen and moisture.

On the other hand, polymorphs are considered as distinct solids because they have different physical properties despite the same molecular formula. Crystalline forms of the compound of Formula 1 are the subjects of U.S. Pat. Nos. 5,969,156 and 6,121,461. Further, PCT International Publication No. WO 01/36384 discloses a polymorphic form of the compound of Formula 1. There is a need in the art for crystalline forms of the compound of Formula 1 that are more stable and easier to handle than the known crystalline forms.

DISCLOSURE OF THE INVENTION

Technical Problem

Therefore, the present inventors intended to develop novel crystalline forms of the compound of Formula 1 that are highly pure, convenient to prepare and highly stable.

Technical Solution

The present invention provides novel crystalline forms D1 and D2 of the compound of Formula 1 and hydrates thereof.

The novel crystalline forms of the present invention will now be described in more detail.

It has been found that the crystalline forms D1 and D2 of the compound of Formula 1 according to the present invention are different from other known crystalline forms of the compound of Formula 1, as determined by X-ray powder diffraction and solid-state $^{13}C$ nuclear magnetic resonance (NMR) techniques.

The X-ray powder diffraction patterns were measured on an M18HF-SRA diffractometer (Mac Science) with CuKα radiation and the $^{13}C$ NMR spectra were recorded on an AVANCE-500 spectrometer (Bruker).

FIG. 1 is an X-ray powder diffractogram of the crystalline form D1, and Table 1 lists 2θ angles, d-spacings and relative intensities with a relative intensity of >10% in the X-ray powder diffractogram.

TABLE 1

| 2θ (°) | d (Å) | Relative Intensity (>10%) |
|---|---|---|
| 5.36 | 16.4745 | 13.4 |
| 7.38 | 11.9689 | 17.0 |
| 7.68 | 11.5022 | 29.6 |
| 8.14 | 10.8531 | 31.7 |
| 8.60 | 10.2733 | 68.6 |
| 8.88 | 9.9503 | 30.4 |
| 10.24 | 8.6312 | 45.3 |
| 12.48 | 7.0867 | 19.7 |
| 13.80 | 6.4115 | 12.7 |
| 17.14 | 5.1691 | 14.5 |
| 17.78 | 4.9844 | 45.3 |
| 18.22 | 4.8651 | 12.8 |
| 18.52 | 4.7870 | 10.1 |
| 19.36 | 4.5811 | 100 |
| 19.96 | 4.4447 | 13.0 |
| 20.76 | 4.2752 | 45.1 |
| 22.40 | 3.9658 | 17.9 |
| 23.20 | 3.8307 | 12.6 |
| 24.18 | 3.6777 | 1.15 |
| 25.62 | 3.4742 | 14.1 |

In addition to the X-ray powder diffraction peaks enumerated in Table 1, the crystalline form D1 may have additional X-ray powder diffraction peaks with weak intensities at 2θ=6.8, 10.8, 14.8, 16.2, 21.8, 25.1, 26.1, 27.2, 27.8, 28.5 and 30.4°.

The peaks with weak intensities are defined to have a relative intensity of <10%. Knowledge about the theory of X-ray powder diffraction patterns can be found in numerous references, for example, X-ray diffraction procedures, H. P. Klug and L. E. Alexander, J. Wiley, New York (1974), well-known in the art to which the technology pertains.

FIG. 2 is a $^{13}$C NMR spectrum of the crystalline form D1 and Table 2 lists chemical shifts for the carbon atoms of the crystalline form D1 in the NMR spectrum.

TABLE 2

| Carbon Atom Assignment | Chemical shift (ppm) |
|---|---|
| C12 or C25 | 179.6 |
| C12 or C25 | 169.1 |
| C16 | 162.5 |
| Aromatic carbons C2-C5, C13-C18, C19-C24, C27-C32 | 140.0, 138.0, 133.8, 131.9, 129.6, 126.0, 119.2, 114.7 |
| C8, C10 | 73.6, 71.2, 69.9 |
| Methylene carbons C6, C7, C9, C11 | 48.0, 45.54, 43.2 |
| C33 | 29.0, 28.6 |
| C34 | 24.2, 22.2 |

*The assigned numbers of the carbon atoms indicated in Table 1 are consistent with those described in Formula 2.

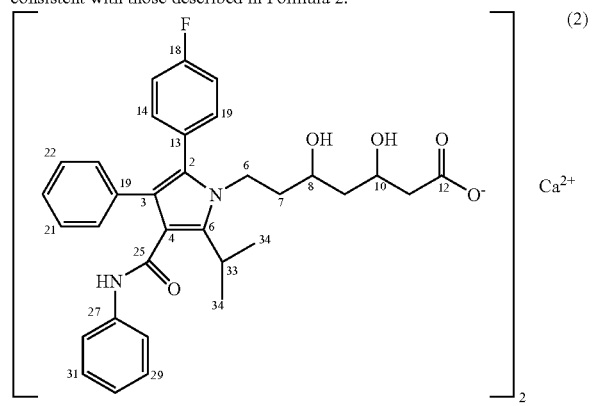

(2)

FIG. 3 is an X-ray powder diffractogram of the crystalline form D2, and Table 3 lists 2θ angles, d-spacings and relative intensities with a relative intensity of >10% in the X-ray powder diffractogram.

TABLE 3

| 2θ (°) | d (Å) | Relative Intensity (>10%) |
|---|---|---|
| 5.56 | 15.8806 | 26.1 |
| 8.54 | 10.3456 | 100 |
| 10.96 | 8.0659 | 10.3 |
| 11.38 | 7.7694 | 36.0 |
| 14.32 | 6.1801 | 11.0 |
| 14.90 | 5.9408 | 11.5 |
| 18.18 | 4.8757 | 37.8 |
| 18.66 | 4.7513 | 29.3 |
| 19.04 | 4.6573 | 18.0 |
| 19.74 | 4.4938 | 20.0 |
| 22.38 | 3.9693 | 10.8 |
| 22.96 | 3.8703 | 14.9 |

In addition to the X-ray powder diffraction peaks enumerated in Table 3, the crystalline form D2 may have additional X-ray powder diffraction peaks with weak intensities at 2θ=9.0 and 11.8° (w).

FIG. 4 is a $^{13}$C NMR spectrum of the crystalline form D2 and Table 4 lists chemical shifts for the carbon atoms of the crystalline form D2 in the NMR spectrum.

TABLE 4

| Carbon Atom Assignment | Chemical Shift (ppm) |
|---|---|
| C12 or C25 | 183.3 |
| C12 or C25 | 170.3 |
| C16 | 164.0 (broad) |
| Aromatic Carbons C2-C5, C13-C18, C19-C24, C27-C32 | 138.1 (broad), 136.0, 131.7, 125.7, 121.8, 120.2 |
| C8, C10 | 73.0 (broad) |
| Methylene Carbons C6, C7, C9, C11 | 44.3 (broad) |
| C33 | 29.1 |
| C34 | 24.6 |

*The assigned numbers of the carbon atoms indicated in Table 3 are consistent with those described in Formula 2.

The present invention also provides hydrates of the crystalline forms D1 and D2. The hydrates of the crystalline form D1 and D2 can contain 0.5-2.5% and 3.5-5.5% of water, respectively. The water contents may vary depending on various factors, such as temperature and relative humidity during storage.

A crystalline form of the compound of Formula has the following advantages over the currently commercially available crystalline form I described in U.S. Pat. No. 5,969,156.

The crystalline form I is produced by reacting a natural form of the compound of Formula 1 (see, Example 10 of U.S. Pat. No. 5,273,995) with a mixture of methanol/water at 40° C. However, crystalline form II is produced when the reaction temperature is lowered to room temperature during the reaction with the methanol/water mixture (see, U.S. Pat. No. 5,969,156). That is, the reaction temperature is a factor determining the crystalline form of the compound of Formula 1. Accordingly, the reaction temperature should be controlled with extreme care in order to obtain a desired pure crystalline form. In contrast, either crystalline form D1 or D2 of the present invention is produced in a pure form over a broad temperature range, including room temperature, thus eliminating the need for careful control of the reaction temperature. For example, the crystalline form I of the compound of Formula 1 is produced at an elevated temperature of 40° C., whereas the crystalline form D2 of the compound of Formula 1 can be produced at room temperature. Therefore, the crystalline form D2 of the compound of Formula 1 is convenient to prepare and has advantages in terms of safety and cost.

The 'natural form of the compound of Formula 1' is prepared in accordance with the procedure described in Example 10 of U.S. Pat. No. 5,273,995 and refers to a state in which amorphous and crystalline forms of the compound of Formula 1 coexist.

Another advantage of the crystalline form D1 is a higher melting point. Specifically, the commercially available crystalline form I has a melting point of ca. 176-178° C. whereas the crystalline form D1 has a melting point of 232° C. This high melting point allows for additional high-temperature processing of the crystalline form D1.

The crystalline form D1 is in the form of a monohydrate and its water content is lower than the crystalline form I in the form of a trihydrate. That is, the number of the molecules present in the crystalline form D1 per unit weight is greater than that of the molecules present in the crystalline form I in the form of a trihydrate, allowing the crystalline form D1 to have better efficacy than the crystalline form I.

The present invention also provides processes for preparing the novel crystalline forms D1 and D2 of the compound of Formula 1.

Specifically, the crystalline form D1 of the compound of Formula 1 can be prepared by dissolving the natural form of the compound of Formula 1 (see, Example 10 of U.S. Pat. No.

5,273,995) in an alcohol/tetrahydrofuran mixture and adding water as an anti-solvent to the solution to crystallize the crystalline form D1. It is preferable to stir the suspension at 0-60° C., particularly 30-50° C., for a long time, particularly 10-72 hours. If needed, seeding can be conducted with the crystalline form D1 during crystallization. It is preferred to use the alcohol, the tetrahydrofuran and the water in a volume ratio of 1:1:8.

The crystalline form D2 of the compound of Formula 1 can be prepared by dissolving the natural form of the compound of Formula 1 in an alcohol/methylene chloride mixture and adding water as an anti-solvent to the solution to crystallize the crystalline form D2. It is preferable to stir the suspension at 0-40° C., particularly 20-30° C., for a long time, particularly 4-48 hours. If needed, seeding can be conducted with the crystalline form D2 during crystallization. It is preferred to use the alcohol, the methylene chloride and the water in a volume ratio of 10:3:30.

The alcohol used in the processes is preferably a $C_1$-$C_6$ lower alcohol. Methanol is most preferred.

The present invention also provides a pharmaceutical composition for reducing the level of low-density lipoprotein (LDL) comprising the crystalline form D1 or D2 or its hydrate as an active ingredient.

The composition of the present invention may further comprise one or more pharmaceutically acceptable carriers. The composition of the present invention may further comprise at least one pharmaceutically acceptable adjuvant or additive selected from excipients, disintegrants, sweeteners, binders, encapsulating agents, swelling agents, lubricants, solubilizers, etc.

The present invention also provides the use of the composition for reducing the level of low-density lipoprotein (LDL) and a method for reducing the level of low-density lipoprotein (LDL) using the composition. Specifically, the method of the present invention comprises administering the composition to a subject in need thereof.

The low-density lipoprotein (LDL) may be one which is present in the blood stream.

The composition of the present invention is useful as an inhibitor of the enzyme 3-hydroxy-3-methylglutaryl-coenzyme A reductase (HMG-CoA reductase) and can be used as a pharmaceutical composition for the treatment and/or prevention of a disease, such as osteoporosis, hyperlipoproteinemia, hypercholesterolemia or Alzheimer's disease.

The present invention also provides a use of the composition for the inhibition of the enzyme 3-hydroxy-3-methylglutaryl-coenzyme A reductase (HMG-CoA reductase). And the present invention also provides a use of the composition for the treatment and/or prevention of a disease, such as osteoporosis, hyperlipoproteinemia, hypercholesterolemia or Alzheimer's disease.

The present invention also provides a method for the inhibition of the enzyme 3-hydroxy-3-methylglutaryl-coenzyme A reductase (HMG-CoA reductase) comprises administering the composition to a subject in need thereof. Specifically, the present invention also provides the method for the treatment and/or prevention of a disease, such as osteoporosis, hyperlipoproteinemia, hypercholesterolemia or Alzheimer's disease, comprises administering the composition to a subject in need thereof.

The composition of the present invention may be formulated into various dosage forms by methods well known in the art, for example, powders, granules, tablets, capsules, suspensions, emulsions, syrups and aerosols for oral administration, external preparations, suppositories, and sterile injectable solutions. Preferably, various formulations of the composition according to the present invention can be prepared depending on the type of diseases to be treated or ingredients known in the pharmaceutical formulation art in accordance with any of the conventional procedures (see, Remington's Pharmaceutical Science, Mack Publishing Company, Easton Pa.). The pharmaceutical composition of the present invention may be administered to mice, rats, livestock and other mammals, including human beings, by various routes. Any mode of administration can be expected. The composition of the present invention can be administered orally, rectally or by injection for example, intravenously, intramuscularly, subcutaneously, intrauterinely, intrathecally or intracerebroventricularly.

A daily dose range of the composition according to the present invention for the reduction of low-density lipoprotein (LDL) or the treatment and/or prevention of a disease, such as hyperlipoproteinemia, hypercholesterolemia osteoporosis or Alzheimer's disease, may typically contain 0.5 to 100 mg and preferably 2.5 to 80 mg of the crystalline form D1 or D2, a hydrate thereof or a mixture thereof. The daily dose may be varied depending upon the type and severity of the disease, age, sex and other relevant factors of the subject, but is generally the same as the known daily dose of the compound of Formula 1.

Advantageous Effects

The crystalline forms of the present invention are purer, more convenient to prepare and more stable than the amorphous forms of the compound of Formula 1.

MODE FOR INVENTION

The following Examples and Experimental Examples are provided to explain the present invention in more detail. However, these examples are given for the purpose of illustration and not intended to limit the present invention.

EXAMPLES

Example 1

Preparation of Crystalline Form D1 of [R—(R*, R*)]-2-(4-fluorophenyl)-β,δ-dihydroxy-5-(1-methylethyl)-3-phenyl-4-[(phenylamino)carbonyl]-1H-pyrrole-1-heptanoic acid hemicalcium salt One gram of a natural form of the compound of Formula 1 prepared in Example 10 of U.S. Pat. No. 5,273,995, was suspended in a mixture of methanol (5 ml), tetrahydrofuran (5 ml) and water (40 ml). The suspension was allowed to react at 30-50° C. for at least ten hours and filtered to obtain a crystal.

Drying of the crystal under vacuum at 40-60° C. for 10-24 hours gave the title crystalline form D1 monohydrate (yield 80%).

Figure 1:
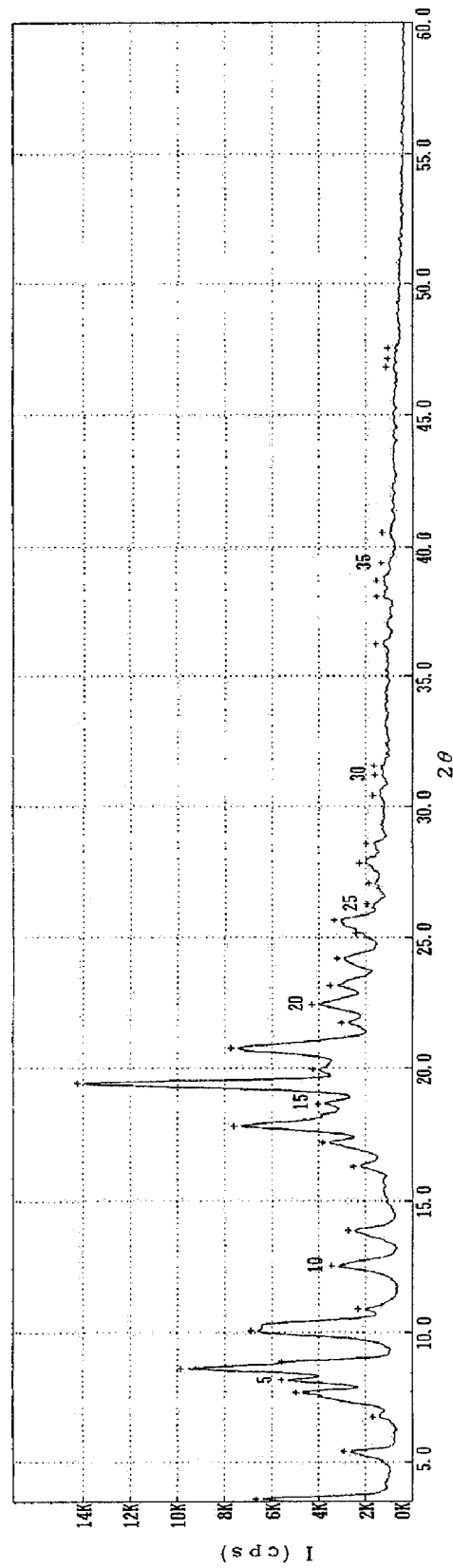
FIG. 1 is an X-ray powder diffractogram of the crystalline form D1 of the compound of Formula 1 according to the present invention.

The X-ray powder diffraction pattern of the product was measured on an M18HF-SRA diffractometer (Mac Science) with CuKα radiation: see, FIG. 1 and Table 1.

Figure 2:
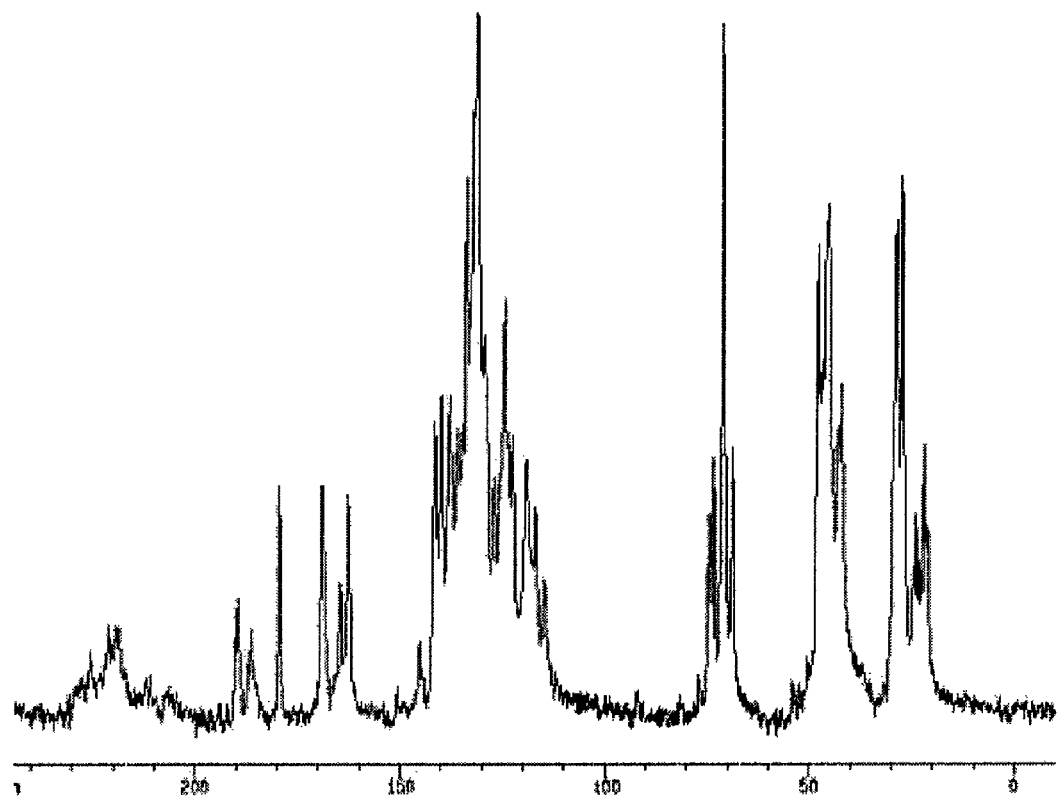
FIG. 2 is a $^{13}$C NMR spectrum of the crystalline form D1 of the compound of Formula 1 according to the present invention.

$^{13}$C NMR (AVANCE-500 Spectrometer (Bruker)): see, FIG. 2 and Table 2.

$^1$H NMR (Varian 400 MHz, DMSO-d6): δ 9.7 (s, 1H), 6.8-7.5 (m, 14H), 4.2 (m, 1H), 3.9 (m, 1H), 3.7 (t, J=6.8 Hz, 2H), 3.4 (m, 1H), 3.3 (s, 3H), 2.5 (d, J=8.0 Hz, 2H), 1.8 (m, 2H), 1.4 (d, J=6.8 Hz, 6H), 1.5 (m, 1H)

Karl fisher (Metrohm 831 KF coulometer): 1.5% (1 mol water)

TGA (sinco TGA N-1000): 1.6% (1 mol water)

Example 2

Preparation of Crystalline Form D2 of [R—(R*, R*)]-2-(4-fluorophenyl)-β,δ-dihydroxy-5-(1-methylethyl)-3-phenyl-4-[(phenylamino)carbonyl]-1H-pyrrole-1-heptanoic acid hemicalcium salt One gram of a natural form of the compound of Formula 1 prepared in Example 10 of U.S. Pat. No. 5,273,995 was suspended in a mixture of methanol (10 ml), methylene chloride (3 ml) and water (30 ml). The suspension was allowed to react at 20-30° C. for at least two hours and filtered to obtain a crystal. Drying of the crystal under vacuum at 40-60° C. for 10-24 hours gave the title crystalline form D2 trihydrate (yield 85%).

Figure 3:
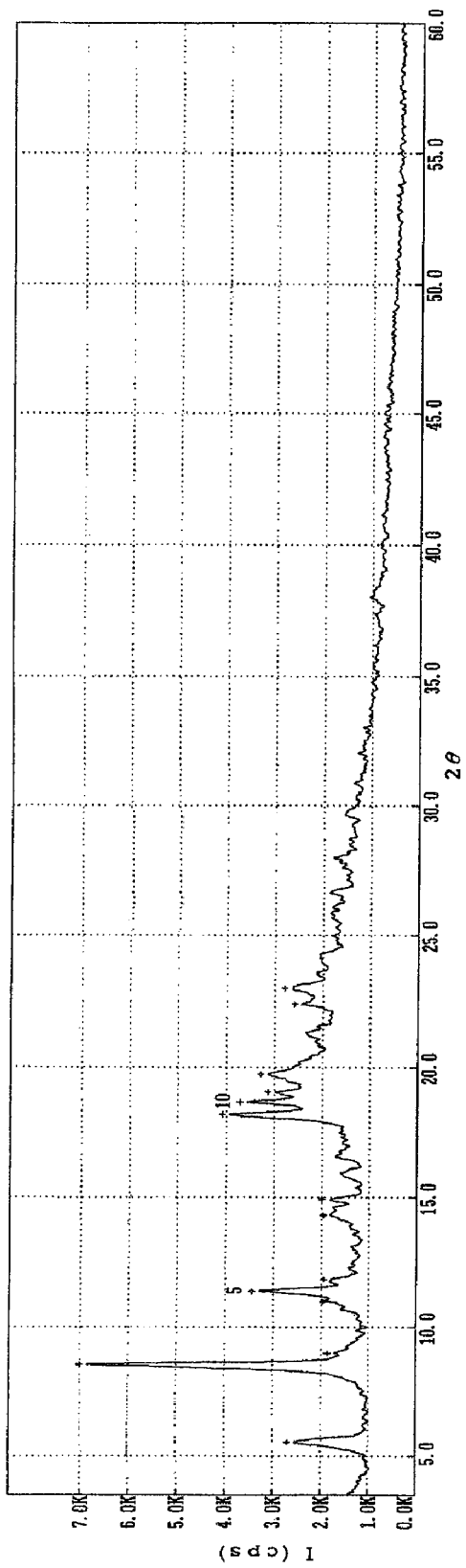
FIG. 3 is an X-ray powder diffractogram of the crystalline form D2 of the compound of Formula 1 according to the present invention.

The X-ray powder diffraction pattern of the product was measured on an M18HF-SRA diffractometer (Mac Science) with CuKα radiation: see, FIG. 3 and Table 3.

Figure 4:
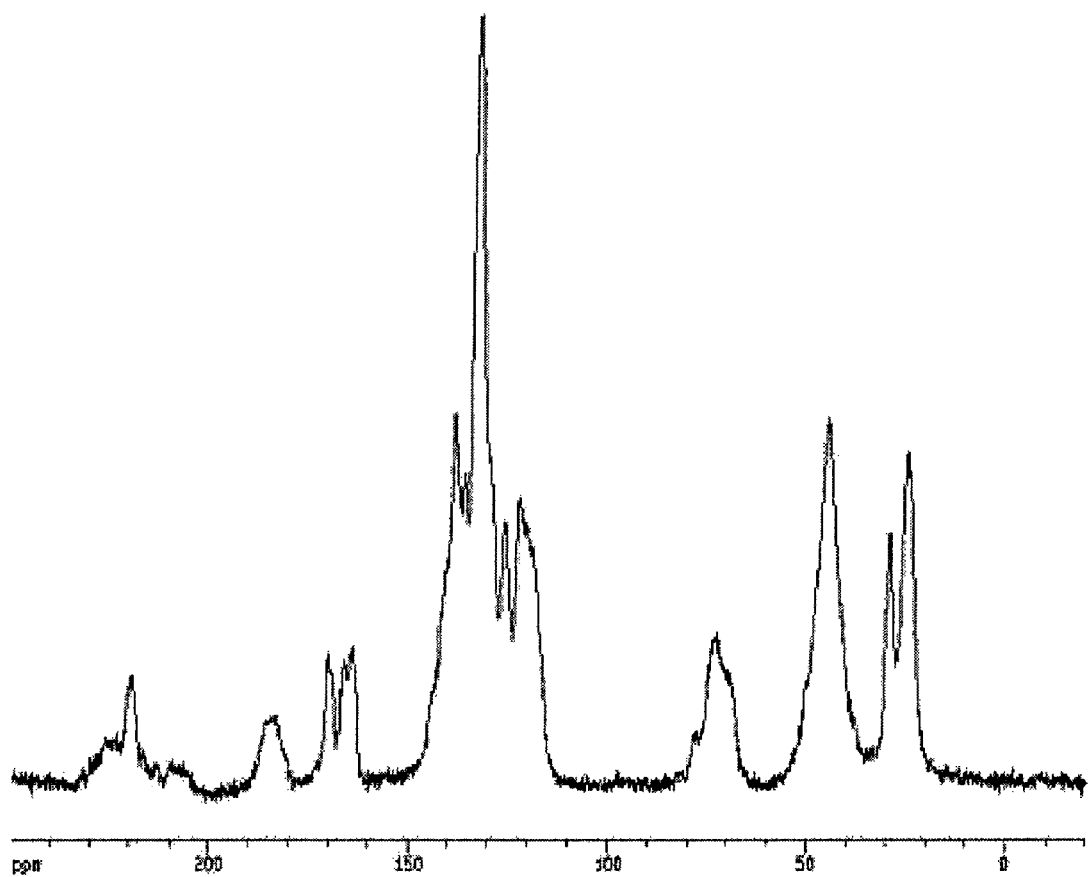
FIG. 4 is a $^{13}$C NMR spectrum of the crystalline form D2 of the compound of Formula 1 according to the present invention.

$^{13}$C NMR (AVANCE-500 Spectrometer (Bruker)): see, FIG. 4 and Table 4.

$^1$H NMR (Varian 400 MHz, DMSO-d6): δ 9.7 (s, 1H), 6.8-7.5 (m, 14H), 4.2 (m, 1H), 3.9 (m, 1H), 3.7 (t, J=6.8 Hz, 2H), 3.4 (m, 1H), 3.3 (s, 3H), 2.5 (d, J=8.0 Hz, 2H), 1.8 (m, 2H), 1.4 (d, J=6.8 Hz, 6H), 1.5 (m, 1H)

Karl fisher (Metrohm 831 KF coulometer): 4.6% (3 mol water)

TGA (sinco TGA N-1000): 4.9% (3 mol water)

Experimental Example 1

Measurement of Melting Points

The melting points of the compounds prepared in Examples 1 and 2 were measured using a Mettler Toledo FP90, and the results are shown in Table 5.

TABLE 5

| Sample | Melting Point (° C.) |
| --- | --- |
| Example 1 | 231.9 |
| Example 2 | 191.7 |

The high melting points of the crystalline forms D1 and D2 allow for additional high-temperature processing of the crystalline forms.

Experimental Example 2

Stability Identification-Content Measurement 80 mg of the novel crystalline form of the compound prepared in Example 2 and 80 mg of a standard product with a purity of 99.9% prepared by the process described in Example 2 were accurately weighed, placed in 100 ml volumetric flasks, and dissolved in dimethylformamide. The volumes of the solutions were adjusted to the marked lines of the flasks to prepare test solutions and standard solutions, respectively. Each of the solutions was analyzed by column chromatography under the following conditions:

Column: Zorbax Rx C8 (4.6 mm×250 mm, 5 μm) or its equivalent

Mobile Phase (0.05 M ammonium acetate buffer (pH=5.0)/acetonitrile/tetrahydrofuran) Mobile Phase A:

0.05 M ammonium acetate buffer (pH=5.0)/acetonitrile/tetrahydrofuran (67/21/12) Mobile Phase B:

0.05M ammonium acetate buffer (pH=5.0)/acetonitrile/tetrahydrofuran (54/34/12)

Detector: UV absorption spectrophotometer (wavelength: 244 nm)

Flow Rate: 1.0 mL/min.

Column Temperature: 35±2° C.

Storage: in HDPE bottle

The contents of the compound prepared in Example 2 were quantified by the area under each peak. Variations in the content of the compound were evaluated at room temperature, in a freezer, under accelerated storage conditions and under extreme storage conditions over the periods indicated in Table 6, and the results are shown in Table 6.

TABLE 6

| 1 | 2 | 3 | 6 |
| --- | --- | --- | --- |
| At room temp. (month) | | | |
| 98.72 | 98.58 | 98.12 | 98.56 |
| In freezer (month) | | | |
| 99.74 | 99.31 | 100.19 | 98.11 |
| 40° C./75% RH (accelerated storage (month)) | | | 60° C./Dry (extreme storage (month)) |
| 1 | 2 | 3 | 1 |
| 98.82 | 98.33 | 98.03 | 98.01 |

From the results in Table 6, it can be seen that the contents of the raw material were maintained after storage for six months at room temperature and in the freezer and the variations in the content of the raw material were stabilized within 98-100.2% even under the accelerated and extreme storage conditions. In conclusion, the crystalline forms of the present invention showed excellent stability.

INDUSTRIAL APPLICABILITY

The crystalline forms of the present invention are purer, more convenient to prepare and more stable than the amorphous forms of the compound of Formula 1.

What is claimed is:

1. A crystalline form (D1) of the compound of Formula 1:

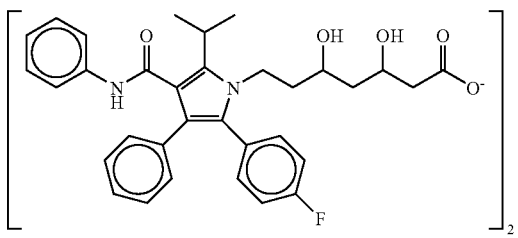

having X-ray powder diffraction peaks at 2θ=5.4, 7.4, 7.7, 8.1, 8.6, 8.9, 10.2, 12.5, 13.8, 17.1, 17.8, 18.2, 18.5, 19.4, 19.9, 20.8, 22.4, 23.2, 24.2 and 25.6°, or its hydrate.

2. The crystalline form D1 or its hydrate of claim 1, wherein the crystalline form D1 has additional X-ray powder diffraction peaks with weak intensities at 2θ=6.8, 10.8, 14.8, 16.2, 21.8, 25.1, 26.1, 27.2, 27.8, 28.5 and 30.4°.

3. The crystalline form D1 or its hydrate of claim 1, wherein the crystalline form D1 exhibits solid-state $^{13}$C NMR signals at about 179.6, 169.1, 162.5, 140.0, 138.0, 133.8, 131.9, 129.6, 126.0, 119.2, 114.7, 73.6, 71.2, 69.9, 48.0, 45.5, 43.2, 29.0, 28.6, 24.2 and 22.2 ppm.

4. A crystalline form (D2) of the compound of Formula 1 having X-ray powder diffraction peaks at 2θ=5.6, 8.5, 10.9, 11.4, 14.3, 14.9, 18.2, 18.7, 19.0, 19.7, 22.4 and 22.9°, or its hydrate.

5. The crystalline form D2 or its hydrate of claim 4, wherein the crystalline form D2 has additional X-ray powder diffraction peaks with weak intensities at 9.0 and 11.8° (w).

6. The crystalline form D2 or its hydrate of claim 4, wherein the crystalline form D2 exhibits solid-state $^{13}$C NMR signals at about 183.3, 170.3, 164.0 (broad), 138.1 (broad), 136.0, 131.7, 125.7, 121.8, 120.2, 73.0 (broad), 44.3 (broad), 29.1 and 24.6 ppm.

7. A process for preparing the novel crystalline form D1 of claim 1, comprising suspending a natural form of the compound of Formula 1 in an alcohol/tetrahydrofuran/water mixture and stirring the suspension at a temperature of 0 to 60° C.

8. The process of claim 7, wherein the alcohol, the tetrahydrofuran and the water are mixed in a volume ratio of 1:1:8.

9. A process for preparing the novel crystalline form D2 of claim 4, comprising suspending a natural form of the compound of Formula 1 in an alcohol/methylene chloride/water mixture and stirring the suspension at a temperature of 0 to 40° C.

10. The process of claim 9, wherein the alcohol, the methylene chloride and the water are mixed in a volume ratio of 10:3:30.

11. The process of claim 7 or claim 9, wherein the alcohol is a $C_1$-$C_6$ lower alcohol.

12. The process of claim 11, wherein the alcohol is methanol.

13. A pharmaceutical composition for reducing the level of low-density lipoprotein (LDL) comprising the crystalline form D1 or D2 or its hydrate according to claim 1 or claim 4 as an active ingredient.

14. A method for reducing the level of low-density lipoprotein (LDL) comprising administering the composition of claim 13 to a subject in need thereof.

* * * * *